(12) United States Patent
Abdellatif et al.

(10) Patent No.: US 10,272,980 B2
(45) Date of Patent: Apr. 30, 2019

(54) UNDERWATER VEHICLES AND INSPECTION METHODS

(71) Applicant: Saudi Arabian Oil Company, Dhahran (SA)

(72) Inventors: Fadl Abdellatif, Thuwal (SA); Ali Outa, Thuwal (SA); Sahejad Patel, Thuwal (SA); Ayman Amer, Thuwal (SA); Hassane Trigui, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/704,718

(22) Filed: Sep. 14, 2017

(65) Prior Publication Data

US 2018/0079476 A1   Mar. 22, 2018

Related U.S. Application Data

(60) Provisional application No. 62/396,937, filed on Sep. 20, 2016.

(51) Int. Cl.
*B63G 8/14* (2006.01)
*B63G 8/00* (2006.01)
(Continued)

(52) U.S. Cl.
CPC ............ *B63G 8/14* (2013.01); *B08B 9/023* (2013.01); *B63B 27/00* (2013.01); *B63B 59/08* (2013.01); *B63G 8/001* (2013.01); *B63G 8/39* (2013.01); *F16L 1/265* (2013.01); *G01N 29/041* (2013.01); *G01N 29/225* (2013.01); *G01N 29/245* (2013.01); *G01N 29/265* (2013.01); *B63G 2008/005* (2013.01); *F16L 55/00* (2013.01); *G01N 2291/0234* (2013.01); *G01N 2291/267* (2013.01)

(58) Field of Classification Search
CPC ........... B63C 11/00; B63C 11/52; B63G 8/00; B63G 8/08; B63G 8/14; B63G 8/22; B63H 1/36; B63H 19/08
USPC ............... 114/222, 312, 330, 331, 332, 333; 405/188, 190, 191
See application file for complete search history.

(56) References Cited

U.S. PATENT DOCUMENTS

| 4,502,407 A | 3/1985 | Stevens | |
|---|---|---|---|
| 4,720,213 A * | 1/1988 | Gernhardt | B63B 59/10 405/188 |

(Continued)

FOREIGN PATENT DOCUMENTS

EP   2762401 A1   8/2014

*Primary Examiner* — Lars A Olson
(74) *Attorney, Agent, or Firm* — Leason Ellis LLP

(57) ABSTRACT

A method for performing operations using a water environment robotic system on a target section of pipeline located in an underwater environment is provided. The method includes the steps of deploying the underwater robotic vehicle into the water and visually inspecting the underwater environment to locate the pipeline and its plurality of weld joints. A cleaning operation is performed at one of the plurality of weld joints using the underwater robotic vehicle. The robotic vehicle can land on the sea floor and deploy a robotic arm to inspect the cleaned weld joint. The underwater can then swim to a next weld joint and land and perform cleaning and inspection operations, which can be repeated until all inspection sites are inspected.

28 Claims, 5 Drawing Sheets

(51) Int. Cl.
  *B08B 9/023* (2006.01)
  *B63B 27/00* (2006.01)
  *B63B 59/08* (2006.01)
  *B63G 8/39* (2006.01)
  *G01N 29/04* (2006.01)
  *G01N 29/24* (2006.01)
  *G01N 29/22* (2006.01)
  *G01N 29/265* (2006.01)
  *F16L 1/26* (2006.01)
  *F16L 55/00* (2006.01)

(56) References Cited

U.S. PATENT DOCUMENTS

| | | | | |
|---|---|---|---|---|
| 4,721,055 A | * | 1/1988 | Pado | B63C 11/52 |
| | | | | 405/188 |
| 6,167,831 B1 | | 1/2001 | Watt et al. | |
| 7,213,532 B1 | * | 5/2007 | Simpson | B63C 11/42 |
| | | | | 114/331 |
| 9,511,831 B2 | * | 12/2016 | Kimura | B63C 11/52 |
| 2009/0114140 A1 | * | 5/2009 | Guerrero | B63C 11/52 |
| | | | | 114/312 |
| 2014/0343728 A1 | | 11/2014 | Jun | |

* cited by examiner

UNDERWATER VEHICLES AND INSPECTION METHODS

CROSS-REFERENCE TO RELATED APPLICATIONS

This application claims priority under 35 U.S.C. § 119 to U.S. Provisional Application Ser. No. 62/396,937, filed Sep. 20, 2016, which is hereby incorporated by reference as if set forth in its entirety herein.

FIELD OF THE INVENTION

A system, method, and devices for performing underwater tasks that includes an underwater robot and reusable buoyancy modules.

BACKGROUND OF THE INVENTION

Inspection of underwater infrastructure, especially in shallow water environments, can be difficult. Shallow water sites (e.g., anything less than or equal to 10 m depth) are difficult to access with sophisticated Diving Support Vessels (DSVs) that are typically used for inspecting underwater pipelines in deeper water with help of tethered divers and/or remotely operated vehicles (ROVs'). Generally, these vessels have a dynamic positioning (DP) system that enables them to stabilize in specific position above the intended targeted inspection sites. A typical DP system only works above 10 m depth of water. Deep water ROVs are equipped with robotic arms and manipulators that can be electrically controlled or using hydraulics and pneumatics. DSVs provide them with electric and mechanical (pneumatic, hydraulics) power, communication, control signals and cleaning fluids (water jet, sand blasting, cavitation jets). As for divers, they are also provided with air, and communication using their umbilical cords tethered to DSVs.

Shallow water environments limit the ability of support vehicles to navigate in close proximity to the structures being inspected. Accordingly, inspection robots need to operate a distance from support vehicles in order to perform inspection and other tasks in these areas. The separation between the support vehicle causes a number of problems with operation of the vehicle, including issues of communication and control over a distance, the need for the robot to travel a distance from the support vehicle to the structure to be inspected, and the ability of the robot to perform inspection and other tasks once the robot is in position.

Accordingly, there is a need to provide underwater vehicles with the means to perform these tasks and an operation method that can be employed to successfully carry out these tasks. Shallow water environment underwater inspection can be achieved according to the present invention as disclosed herein.

SUMMARY OF THE INVENTION

In one aspect of the invention, a method for performing operations on underwater infrastructure at a plurality of locations using a water environment robotic system is provided. The method includes the steps of providing an underwater robotic vehicle at a position proximate the underwater infrastructure. The underwater robotic vehicle is moved through the water to one location of the plurality of locations of the underwater infrastructure. A first operation is performed on the underwater infrastructure at the one location of the plurality of locations. The underwater vehicle is manipulated to engage with a subsea surface. A second operation is performed on the underwater infrastructure at the one location of the plurality of locations. The underwater robotic vehicle is moved through the water to another location of the plurality of locations of the underwater infrastructure. The steps of performing the first operation through moving the vehicle to another location is repeated until all desired operations are performed at all of the desired locations of the plurality of locations. The method further includes the step of retrieving the underwater vehicle.

According to a further aspect, the first operation is a cleaning operation and the second operation is an inspection operation of the previously cleaned first location using a non-destructive sensor.

According to a yet further aspect, the underwater infrastructure is a pipeline and the plurality of locations are weld joints along the pipeline.

According to a further aspect, the step of manipulating the underwater vehicle to engage with a subsea surface includes the step of controlling and manipulating a buoyancy module to change the buoyancy characteristics of the underwater vehicle from neutrally buoyant to negatively buoyant.

According to a still further aspect, the step of performing a second operation includes the steps of extending a robotic arm and sensing using a non-destructive sensor.

According to a yet further aspect, the step of moving the underwater robotic vehicle through the water to another location includes the step of reengaging the underwater vehicle with a buoyancy module to change the buoyancy characteristics of the underwater vehicle from negatively buoyant to neutrally buoyant and moving through the water.

According to another further aspect of the invention, a method for performing operations using a water environment robotic system on a target section of pipeline located in an underwater environment is provided. The pipeline has a plurality of weld joints located at a plurality of locations along its length. The method includes the steps of providing an underwater robotic vehicle at a position proximate the underwater pipeline. The underwater robotic vehicle includes at least a robotic arm, treads adapted to move the underwater robotic vehicle along a subsea surface, a sensor, and a propulsion system adapted to move the underwater robotic vehicle by swimming through the water. The method includes the step of deploying the underwater robotic vehicle into the water. The underwater environment is visually inspected to locate the pipeline and its plurality of weld joints using the underwater robotic vehicle. A cleaning operation is performed at one of the plurality of weld joints using underwater robotic vehicle. The underwater robotic vehicle is manipulated to land and stabilize on a subsea surface. The position of the underwater robotic vehicle is adjusted on the subsea surface. The robotic arm is deployed to inspect the cleaned weld joint and the cleaned weld joint is inspected using the sensor to collect cathodic protection and ultrasonic testing data. The robotic arm is stowed into a folded position suitable for the underwater robotic vehicle to swim through the water and the underwater robotic vehicle swims through the water along the pipe line to another of the plurality of weld joints while performing a visual inspection. The steps of cleaning through swimming to a next location are repeated on multiple weld joints within the target section of the pipeline. The method further includes the steps of causing the underwater robotic vehicle to swim upward and permitting retrieval of the underwater robotic vehicle at a surface of the water environment.

According to a further aspect, the step of deploying the underwater robotic vehicle into the water includes deploying the underwater robotic vehicle from a surface support vessel.

According to a yet further aspect, the step of deploying the underwater robotic vehicle into the water includes deploying the underwater robotic vehicle from an onshore location and using the treads to crawl along the subsea surface until the underwater robotic vehicle moves to a position in which the water has a sufficient depth to permit swimming of the underwater robotic vehicle.

According to a still further aspect, the underwater robotic vehicle is connected to a communication relay that is configured to permit aerial communication between the underwater robotic vehicle and a remote control station.

According to a yet further aspect, the method further includes the step of locating the pipeline using a sonar sensor mounted below the surface support vessel.

According to a further aspect, the method further includes the step of locating the pipeline using a sonar sensor mounted on the underwater robotic vehicle.

According to a still further aspect, the step of performing a cleaning operation includes using at least one of a cavitation system and a brushing system.

According to a yet further aspect, the cavitation system includes a cavitation engine supported by a surface boat.

According to a still further aspect, the brushing system includes systems having destabilization reduction means for reducing forces caused during the step of performing a cleaning operation.

According to a yet further aspect, the step of manipulating the underwater vehicle to land and stabilize on a subsea surface includes engaging the propulsion system to provide a downward force toward the subsea surface.

According to a further aspect, the step of adjusting the position of the underwater robotic vehicle on the subsea surface includes using propellers.

According to a still further aspect, the step of adjusting the position of the underwater robotic vehicle on the subsea surface includes using the treads to minimize disturbance to the underwater environment.

According to a yet further aspect, the underwater robotic vehicle includes a buoyancy control module, and wherein the step of manipulating the underwater robotic vehicle to land and stabilize on a subsea surface includes using the buoyancy control module to provide the underwater robotic vehicle a negative net buoyancy characteristic.

According to a further aspect, the buoyancy control module includes at least one of a releasable float device, a container in which air is capable of being compressed, and a container into which air and water is capable of being introduced and removed.

According to a further aspect, the underwater robotic vehicle has a negative net buoyancy characteristic sufficient for stabilization on the subsea surface and also sufficient for swimming through the water using the propulsion system.

According to a further aspect, the underwater robotic vehicle includes a buoyancy control module, the method further including the step of using the buoyancy control module to provide the underwater robotic vehicle a net neutral buoyancy characteristic prior to the step of swimming through the water along the pipe line to another of the plurality of weld joints.

According to a further aspect, the underwater robotic vehicle includes a first video camera.

According to a still further aspect, the underwater robotic vehicle includes a second video camera supported by the robotic arm to provide improved monitoring of the inspection sensor.

According to a yet further aspect, the underwater robotic vehicle includes at least one of a proximity sensor and a sonar sensor, supported by the robotic arm.

According to a yet further aspect, the underwater robotic vehicle supports a cleaning module and an inspection module.

According to a further aspect, the underwater robotic vehicle includes first and second underwater robotic vehicles, wherein one of the first and second underwater robotic vehicles executes the step of performing a cleaning operation at one of the plurality of weld joints, and the other of the first and second underwater robotic vehicles executes the step of inspecting the cleaned weld joint using the sensor to collect cathodic protection and ultrasonic testing data.

These and other aspects, features, and advantages can be appreciated from the accompanying description of certain embodiments of the invention and the accompanying drawing figures and claims.

DETAILED DESCRIPTION CERTAIN OF EMBODIMENTS OF THE INVENTION

Figure 1:
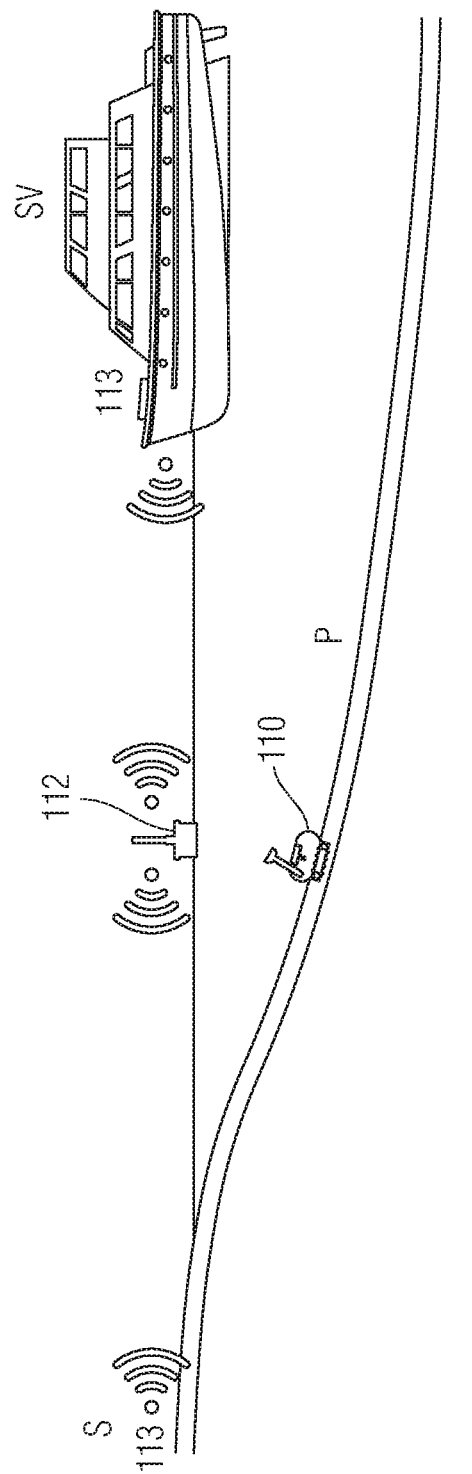
FIG. 1 show details of the system in accordance with one embodiment of the present invention.

Referring to FIG. 1, an aquatic environment robotic system 100 is shown. A pipeline P is an example of target infrastructure that is to be operated upon by an underwater robotic vehicle 110. The section of the pipeline P to be operated upon is located in shallow water. A support vessel SV is located near the section of the pipeline P that is to be operated upon, but is prevented from being positioned directly over the area to be inspected because of the shallow depth of the water. Accordingly, the support vessel SV is located in deeper water a distance from the target area of the pipeline. The underwater robotic vehicle can be launched from the SV and travel to the area of the pipe to be inspected. Alternatively, the underwater robotic vehicle 110 can be deployed from the shore S and move through the water to arrive at the area of the pipe P to be inspected. As such, a control station 113 can be located on the support vessel SV and/or shore S and can depend on whether the underwater vehicle 110 is launched from a support vessel and/or the shore.

The underwater robotic vehicle 110 can include a surface boat 112 that can remain on the surface of the water. The surface boat 112 can act as a relay between the control station 113 (e.g., support vessel SV and/or the shore S) and the underwater robotic vehicle 110. Communication and control signals can be sent from the control station 113 which are received by the surface boat 112. The surface boat 112 can then relay the signals to the underwater robot 110. The signals can be used to command and control the operation of the underwater robotic vehicle 110. Similarly, the underwater robotic vehicle 110 can send signals (e.g., feedback, position, inspection results, etc.) back to the surface vehicle 112 which are then relayed back to the control station 113.

Referring to FIGS. 2A-2C, the underwater robot 110 and the surface vehicle 112 are shown in various configurations that allow the vehicle to alter it buoyancy configuration so that it can perform various operations underwater more efficiently. As shown in FIG. 2A, the surface vehicle 112 and the underwater robot 110 are engaged and the two vehicles have a neutral net buoyancy. The surface vehicle 112 can have a positive buoyancy and the underwater vehicle 110 can have a negative buoyancy, but when the two vehicles are engaged with each other, the buoyancy forces are transferred between the two vehicles and results in a net neutral buoyancy.

Figure 2:
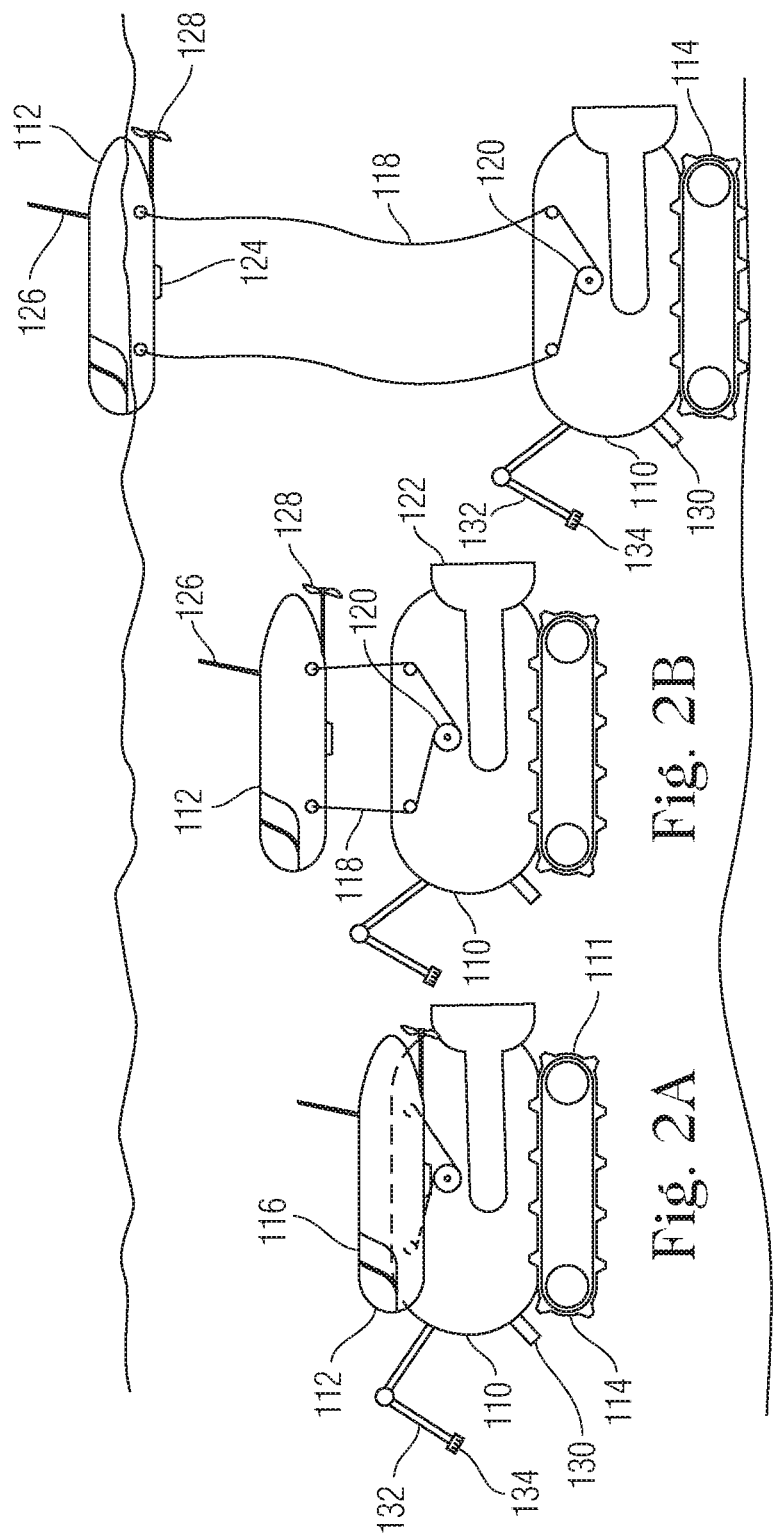
FIGS. 2A-2C show details of the system in various operational states underwater.

The underwater robot 110 can include a lower body portion 111. The main hull of the underwater robot 110 can house various electronics, motors, thrusters, sensors, and power sources, as determined as necessary for a particular operation of the robot. The lower body portion 111 can include tracks or treads 114, as shown in FIG. 2, that can be used to traverse the subsurface floor.

The surface vehicle 112 functions as a buoyancy module 116 and is connected to the underwater robot 110 via tethers 118. The underwater robot 110 includes a motorized pulley or winch system 120. The surface vehicle 112 can be connected to the underwater robot 110 via one or more tethers 118. The winch system 120 includes a motor and a pulley or drum that are configured to extend and retract the tethers 118. The winch system 120 includes a motor and drum or pulley to wind and unwind the tethers 118. For example, when the motor of the winch system 120 rotates in a first direction, the tethers 118 unwind and extend from the underwater robot. When the motor causes of the drum to rotate in opposite direction, the tethers 118 wind onto the drum and retract into the underwater robot. By the mode of operation, the winch system 120 can extend and retract the tethers 118 upon receiving an input control command. A state control device, such as a processor receiving and providing commands or an electrical or mechanical user input device, can be connected to the winch to control the operation of the winch, which, in turn, operates to transition the robotic system between at least two buoyancy states, as discussed in more detail below.

As the tethers 118 extend and/or retract by operation of the winch 120, the surface vehicle, which is connected to the tethers 118, also extends and retracts, respectively. In FIG. 2A, the tethers 118 are in a retracted position, that is, the tethers 118 are wound about the drum of the winch system 120, and the surface vehicle 112 is engaged with the underwater robot 110. Accordingly, the tethers 118 are under tension and are transmitting that buoyancy force to the underwater robot.

In FIG. 1B, the winch system 120 is shown in the process of deploying the surface vehicle 112, which includes buoyancy module 116, by extending the tethers 118 so that the buoyancy module is extended away from the underwater robot 110. Due to the positive buoyancy of the buoyancy module 116, the buoyancy module 116 rises through the water column towards the surface of the water. However, the tethers 118 are still under tension and so the buoyancy force is still transferred to the underwater robot 110 through the tethers 118 in configuration shown in FIG. 2B. As such, the buoyancy module 116 is still engaged with the underwater robot 110 in this configuration because the tethers 118 are under tension and exerting force on the underwater robot 110.

In FIG. 2C, the winch system 120 has unwound and extended enough length of the tethers 118 so that the surface vehicle 112 (including buoyancy module 116) has risen through the water column to the surface of the water and the underwater robot has descended through the water column to make contact with the underwater surface. In this condition, the tethers 118 have been extended to an extent so that the buoyancy force is no longer being transferred through the tethers 118. As shown in FIG. 2C, the surface vehicle 112 (with buoyancy module 116) is freely floating on the surface of the water and the underwater robot is resting on the undersea surface. The tethers 118 have been extended a length greater than the water column, i.e., greater than the depth of the water in that location, so that the tethers 118 have become slack with respect to the buoyancy module 116 and the underwater robot 110. In this configuration, the buoyance module 116 is disengaged from the robot 110 because the buoyance module is no longer exerting a buoyance force on the robot 110.

In the slack condition, the tethers 118 are no longer transferring the buoyance force to the robot 110. As a result of the tethers 118 no longer transferring the buoyancy force to the underwater robot 110, the net buoyance of the underwater robot 110 has increased. As such, the underwater robot 110 experiences a greater gravitational force which holds it against the undersea surface. The increased net downward force experienced by the underwater robot 110 increases the traction between the underwater robot 110 and the undersea surface. The increased traction allows the robot to travel along the undersea robot in a more stable manner because better traction is maintained. Moreover, this increased traction allows the underwater robot 110 to perform tasks more efficiently because the underwater robot has a greater stability. For example, if the underwater robot 110 were operated to remove fouling from a pipe surface, the force exerted by the fouling removal tool against the pipe would result in an equal and opposite force against the underwater robot 110. As such, there is a tendency for the underwater robot 110 to be pushed away from the pipe as it applies force on the pipe. The increased traction of the underwater robot 110, caused by the reduced buoyancy as a result of the disengagement of the buoyancy module 116, resists this force and allows the robot to stay in the desired position during the cleaning operation.

Accordingly, the mobile robot system 10 can be reconfigured to adjust the buoyancy characteristics of the underwater robot 110 during certain operations and to be adjusted again during other operations, as required.

For example, when the robot system is first deployed into the water, it may be desirable to have the surface vehicle 112 (with buoyancy module 116) engaged with the underwater robot 110, as shown in FIG. 2A. The neutral buoyancy achieved by the engagement of the buoyancy module 116 and the underwater robot 110 improves the efficiency of swimming through the water column and permits the use of thruster 122 to move the robot through the water column. The thrusters 122 can be used to move the robot to a desired position. Once at the desired position, the winch 120 can be activated to extend the tethers 118 to a sufficient extent such that the buoyancy module 116 is floating on the surface of the water and the underwater robot 110 is resting against the subsea surface with sufficient slack in the tethers 118, as shown in FIG. 1C. Once the buoyance module 116 has been disengaged from the underwater robot 110 (i.e., the no force is exerted by the buoyancy module on the underwater robot), the underwater robot 110 has a negatively buoyant condition which is suitable for traversing (i.e., using treads 114 or other means (e.g., crawler legs, propellers, thrusters)) and operating (performing inspection, cleaning, maintenance operations, etc.) on the undersea surface. The tracks/treads 114 can be used to reduce the disturbance of sand/silt in the undersea environment, especially in extremely shallow waters, as compared to certain uses of propellers and thrusters. The disruption of sand and silt can reduce visibility in the undersea environment, which can negatively impact operation of the vehicle. After the crawling or other operations conducted on the sea surface are complete, the winch 120 can wind up and retract the tethers, thereby reengaging the buoyance module 116 and the underwater robot 110 (i.e., force is exerted by the buoyancy module on the underwater robot). In this way, after the subsea floor operations are complete the underwater robot is now again neutrally buoyant and can move through the water column in an efficient manner. Once operations are complete, the underwater robot 110 can swim to the surface for retrieval from the water.

Accordingly, in a first condition the underwater robot can have a first buoyancy, in a second condition it can have a second buoyancy, and in the third condition it can have third buoyancy. For example, in the first condition the underwater robot has a neutral buoyancy characteristic, in the second condition the underwater robot has a negative buoyancy characteristic, and in the third condition the underwater robot has a neutral buoyancy characteristic.

As such, the buoyancy of the underwater robot can be changed using mechanical devices such as winches and tethers. The use of a winch and tether system provides a cost-effective and efficient means of controlling the buoyancy of the vehicle as compared to other systems that require the changing of hydraulic ballast. Moreover, since the buoyancy module remains connected to the underwater vehicle by tethers, the buoyancy module can be recovered and reused after it is disengaged from the underwater robot. This offers significant advantages over typical drop-ballast systems in which ballast material is simply released and disregarded and cannot be reused. Moreover, the ability to engage, disengage, and reengage the buoyancy module permits the buoyance of the robot to be adjusted multiple times throughout an operation. This permits greater flexibility and operation complexity to be achieved with a single launch of the robot. For example, the robot can swim to a first location, land on the seafloor to perform an operation, reengaged with the buoyance module so that it can swim to another location, and then land again to perform a second operation. The can be repeated many times before the robot ultimately resurfaces for retrieval from the water.

As noted above, the arrangement shown in FIG. 2 incorporates a positively buoyant surface vehicle 112 (and buoyancy module 116). In addition, negatively buoyant and/or neutrally buoyant buoyancy modules can also be used in other arrangements, as discussed in more detail below. The buoyancy of the buoyancy module can be adjusted by adjusting the density of the material of the buoyancy module and/or adjusting the volume of the buoyancy module. For example, the buoyancy module can be an air filled bladder, or a bladder filled with foam oil or other material that has a density lower than water. A buoyancy module incorporating lower density materials will result in a positively buoyant module. Similarly, a buoyancy module that incorporates denser materials, such as lead weights, sand rocks, or other materials that are denser than water, will result in a negatively buoyant buoyancy module.

As discussed above, the underwater vehicle 110 and the surface boat 112 are connected via tethers 118. When the tethers 118 are under tension, buoyancy force is transferred between the vehicles through the tethers 118 and the vehicles are engaged. When the tethers 118 are no longer under tension, for example, when the tethers have been extended so that the surface vehicle 112 is on the surface of the water and the underwater vehicle 110 in on the subsea floor and the tethers 118 are slack, as shown in FIG. 2C, buoyancy force is no longer transferred through the tethers 118 and the two vehicles are disengaged.

The surface vehicle 112 can also include communication relay 126 that can receive communications over the air from the remote control station 113 and then relay those signals to the underwater robot 110, either wirelessly through the water or through a communication tether (not shown). The communication relay 126 can be, for example, a buoy, robotic boat, or zodiac. The connection between the communication relay and the vehicle can be wired (e.g., fiber optic and/or electrical tether) or use an underwater wireless technology (e.g., laser, LED, RF, acoustic etc.). The surface vehicle 112 can also include a position sensor 124 for tracking the relative position of the underwater robot 110 to the surface vehicle 112. The surface vehicle 112 can also include processors for calculating the relative position of the two vehicles and can further include a propulsion system 128 that can be commanded to move the surface vehicle 112 so that a relative positioning is maintained between the underwater robot 110 and the surface vehicle 112 as the underwater robot performs its various operations.

The underwater robotic vehicle 110 can include a first tool 130. The underwater robotic vehicle 110 can include a robotic arm 132 and a second tool 134 supported on the distal end of the robotic arm 132. The first tool 130 can be a cleaning tool that can be used to remove debris from an underwater target structure such as pipeline P. The cleaning tool can be a brush type tool and/or a jet type cleaning tool that blasts high pressure water (which can include a sand slurry) to remove debris. The second tool 134 can be an inspection tool that can be used to inspect the pipe after it has been cleaned. The inspection tool can be a cathodic protection (CP) voltage and measuring surface thickness using ultrasonic testing (UT), as discussed in more detail below. However, other types of inspection tools, such as cameras, sensors, or non-destructive testing devices can be used.

Figure 5:
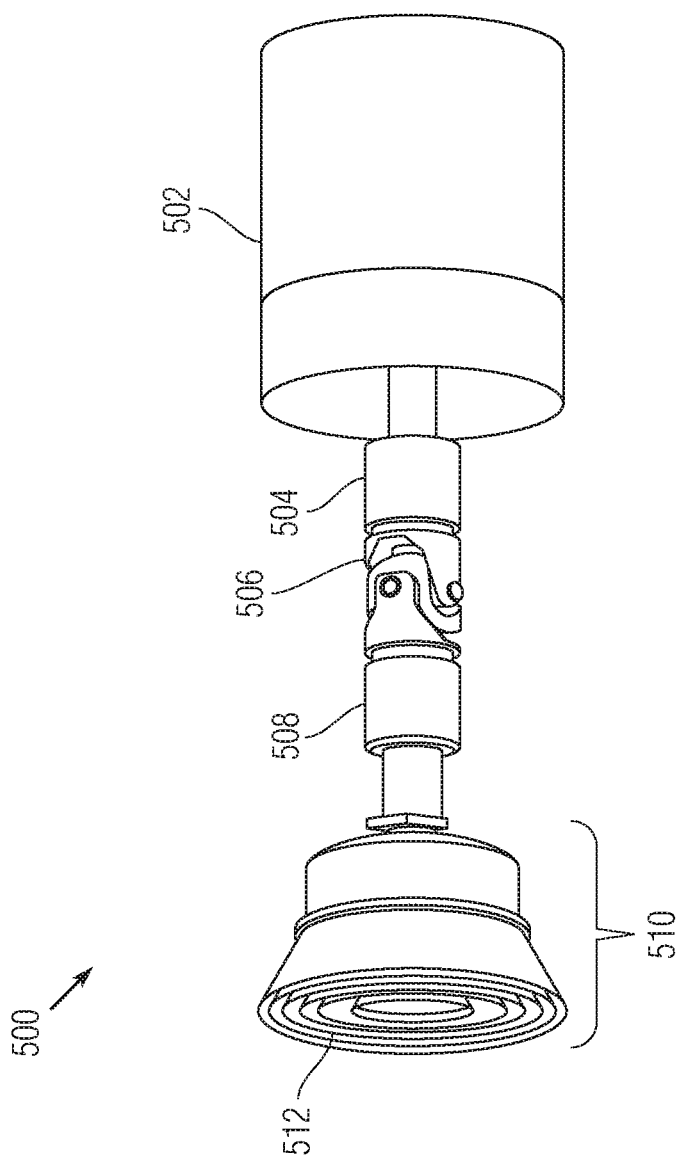
FIG. 5 shows an exemplary cleaning tool.

As one example, the cleaning tool can be a cleaning device 500, as shown in FIG. 5. A motor 502 disposed in a housing is attached to a proximal end of a rotatable first shaft 504 that extends longitudinally along a first axis. The motor provides power to rotate the first shaft around the first axis. The distal end of the first shaft 504 is coupled to a universal joint 506. The universal joint 506 can be any conventional universal joint known in the art (e.g., a Cardan or Hooke type) that can transfer rotational power (e.g., speed and torque) between two shafts while providing at least two degrees of freedom of movement (e.g., rotational motion and angular motion). In the example cleaning device 500, the universal joint 506 is also coupled to a proximal end of a rotatable second shaft 508 that extends longitudinally from the universal joint along a second axis. The universal joint 506 enables the second shaft 508 to receive rotational motion of the first shaft 504 such that the second shaft can rotate about the second axis and also so that the second shaft can angularly displace (i.e., pitch) about a rotational axis having a center point at the universal joint. As the second shaft 508 pitches about the rotational axis, an angle is created between the first shaft 504 and the second shaft 508. This angle can be restricted by the type of universal joint 506 chosen.

A cleaning mechanism 510 having a cleaning face 512 is coupled to a distal end of the second shaft 508. The cleaning mechanism 510 receives the rotational motion of the second shaft 508 about the second axis, which in turn enables a cleaning face 512 to rotate in a plane substantially perpendicular to the second axis. The cleaning face 512 can, for example, include cleaning instruments such as brushes, bristles, or water jets. As the cleaning face 512 rotates, the cleaning instruments contact the target surface and remove biofoul. In one or more implementations, the motor 502 can provide power to change the rotation direction of the cleaning device 500 components (e.g., from clockwise to counter-clockwise and vice versa). Alternating rotational direction allows, for example, a cleaning face 512 having brushes to alternatively scrub the target surface in both rotational directions, thereby enhancing efficiency of the cleaning. This motion can be achieved mechanically (e.g., via a crank shaft) or controlled electrically.

The cleaning device 500 can passively align a cleaning mechanism to a curved, non-uniform, or irregular underwater surface to provide enhanced cleaning performance and minimize destabilizing effects on the underwater vehicle 110. The cleaning device 500 provides the advantage of being able to adapt to the contour of curved surfaces, such as, for example, pipelines, risers, or boat hulls. In one aspect, the cleaning device 500 has one or more degrees of freedom of movement for aligning the cleaning mechanism substantially transverse to a target surface. The cleaning device can include an alignment mechanism to minimize traction and gravitational forces, and thereby reduce or minimize destabilizing effects. More specifically, the alignment mechanism can restrict the cleaning mechanism's motion to a specified range in order to minimize such traction and gravitational forces and maximize stability of the underwater vehicle. In certain embodiments, a cleaning mechanism can have cleaning instruments such as brushes, bristles, or water jets. The cleaning mechanism can also include a plurality of concentric brushes that are capable of spinning in alternate directions using a planetary gears system.

In one or more implementations, the cleaning device 500 can include an adhesion component to enhance its passive self-orienting capabilities. For example, the cleaning mechanism 510 or cleaning face 512 can be magnetized (e.g., via a rare earth magnet like neodymium or an electromagnet) to assist in guiding the transverse orientation of the cleaning face to ferromagnetic curved surfaces such as pipes. In one or more implementations, the adhesion component can include suction mechanisms for guiding the cleaning face toward non-ferromagnetic target surfaces. The cleaning device 500 is just one example of a cleaning tool and other cleaning tools can be used in combination with the underwater robotic vehicle 110.

As discussed above, in certain embodiment's the inspection tool be an integrated probe for measuring cathodic protection (CP) voltage and measuring surface thickness using ultrasonic testing (UT) in which the delay between taking each measurement is minimized. In this way, CP and UT measurements can be performed substantially simultaneously. For example, both CP and UT measurements can be performed during a single touchdown at a specific underwater surface (or an "inspection surface"), such as an underwater pipeline or piling, or the underside of a moored ship hull.

In one aspect, the second tool 134 can be integrated probes can be coupled to a robotic arm 132 of the underwater vehicle 110. In one or more embodiments, the integrated probe system includes a central UT sensor or transducer (e.g., a piezo-ceramic crystal) with a surrounding array of electrically conductive legs having tips or fixtures that are articulated and passively adjustable. The electrically conductive legs are not rigid, but rather have some flexibility with respect to how they contact an underwater surface. In this way, when the electrically conductive legs contact an underwater surface, they passively adjust to orient the UT sensor transverse to the inspection surface. At the same time, the legs conduct the cathodic protection electrical voltage associated with the surface, such as with electrically conductive steel tips, thereby acting as a CP probe. In this way, CP and UT measurements can be conducted substantially simultaneously, thereby reducing measurement inspection time, the size and weight added to the robotic arm, and improving ROV agility.

In addition, embodiments are provided that are directed to magnetically coupling integrated probes and integrated probe systems for measuring cathodic protection (CP) voltage and measuring surface thickness using ultrasonic testing (UT) in which the delay between taking each measurement is minimized. In this way, CP and UT measurements can be performed substantially simultaneously. For example, both CP and UT measurements can be performed during a single touchdown at a specific underwater surface (or an "inspection surface"), such as an underwater pipeline or piling, or the underside of a moored ship hull.

During touchdown, in order to counteract the recoil force created by contact between the integrated probe and the inspection surface, the integrated probe systems include magnetic adhesion components that serve to magnetically couple the integrated probe to the inspection surface. Typical inspection surfaces, such as pipelines, comprise ferromagnetic materials (e.g., iron, cobalt, steel, or nickel) or include cathodic protection coating (e.g., zinc, magnesium, aluminum) that is made electromagnetically receptive by connecting the surface to a sufficient current.

Integrated probe systems herein provide the advantage of being implementable by small, lightweight class ROVs having only a single robotic arm, such as electric ROVs, general class ROVs, inspection class ROVs, and observation class ROVs. Smaller class ROVs are advantageously deployable for inspection surfaces having accessibility issues (e.g., shallow water sites), or if there are power supply limitations.

Figure 3:
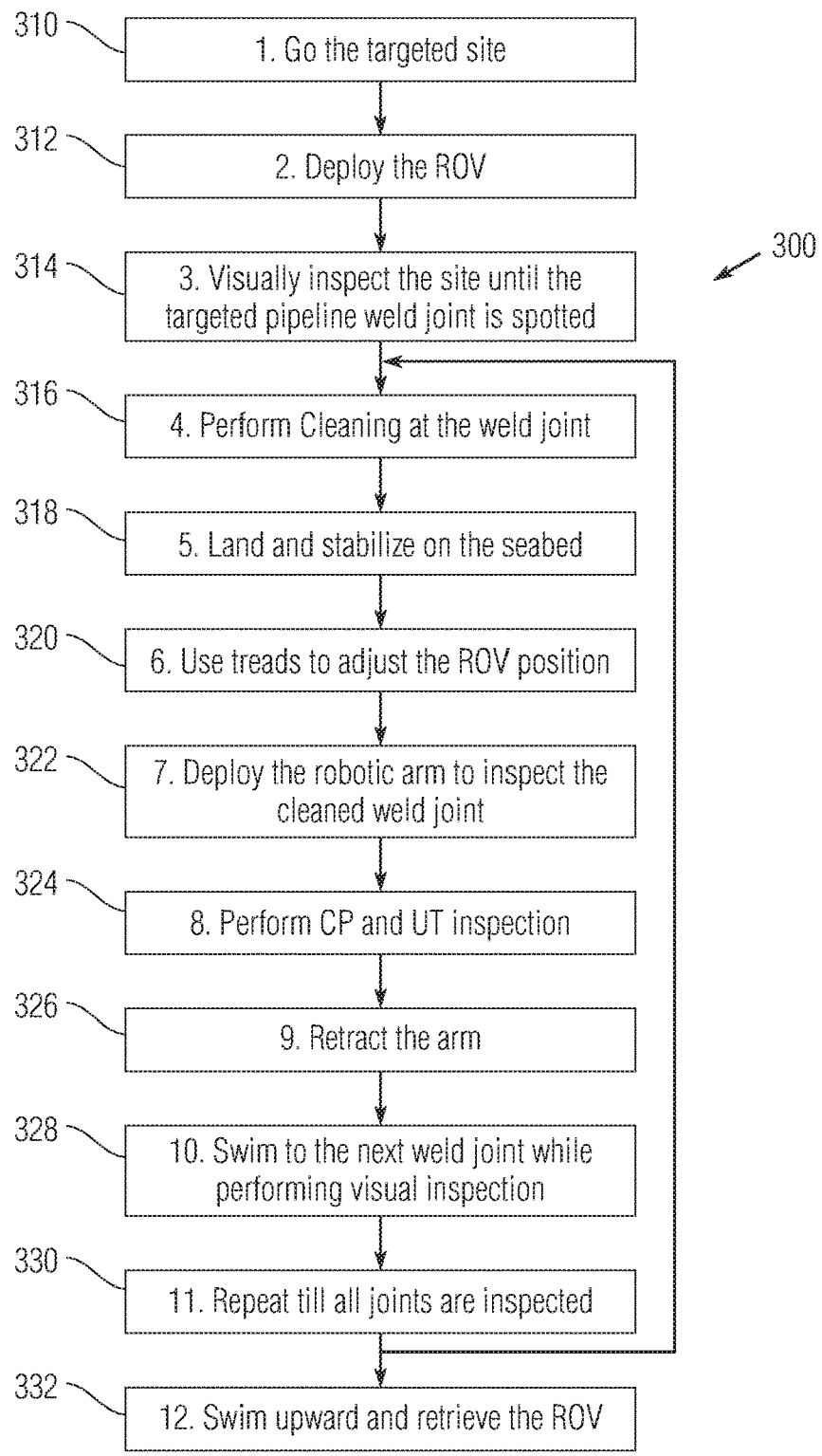
FIG. 3 shows a flow chart detailing operational steps according to an embodiment of the present invention.

Accordingly, the above described robotic systems can be employed in a method according to the present invention to effectively inspect underwater infrastructure. Referring to FIG. 3, a flow chart 300 is provided that illustrates an embodiment of the inspection method.

According to steps 310 and 312, the underwater robotic vehicle 110 (remotely operated vehicle (ROV)) is brought to a location that is in proximity to the target structure to be inspected and then is deployed into the water. The underwater vehicle 110 can be brought to the shore S close to the inspection site and/or brought via the support vehicle SV and deployed from the shore S or support vehicle SV. If the underwater vehicle 110 is deployed from the shore S, it can crawl on the seabed using tracks 114 until it has entered water that is deep enough to start swimming. The underwater vehicle 110 can include a surface vehicle 112 that can act as a relay. The underwater vehicle 110 can swim near the surface or with the surface vehicle partially extended (as in FIG. 2B, for example) so that the surface vehicle 112 can act as a relay while the underwater vehicle swims to the desired location.

Figure 4:
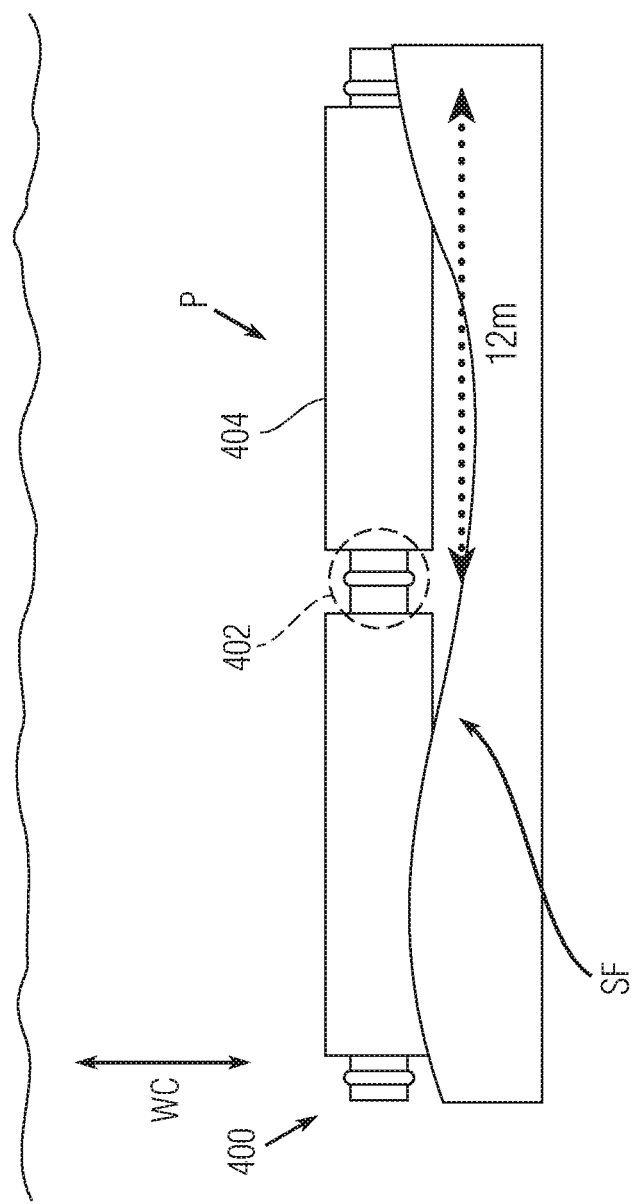
FIG. 4 shows an exemplary pipeline.

According to step 314, once the underwater vehicle is in proximity to the target structure, a visual inspection (e.g., using on board video cameras) can be performed to confirm that the robot is in the correct position with respect to the target structure to perform operations on the target structure. For example, the target structure can be a weld joint on an underwater pipeline P. Turning briefly to FIG. 4, that figure shows an exemplary target section of pipeline P that can include sections of pipe 400 connected by weld joints 402. A concrete weighted jacket 404 can be provided on the sections of pipe 400 to weigh the pipeline down and maintain it in contact with the subsea floor SF. As discussed in more detail below, the underwater robotic vehicle can perform various operations on the pipeline while swimming in the water column WC and/or while landed on the subsea surface SF.

At step 316, an operation can be performed on the underwater target structure. For example, the first tool 130 can be a cleaning tool (e.g., brush, cleaning jet, cavitation jet/engine, etc.) that can be used to clean the weld joint of the underwater pipeline. It is believed that using cavitation to perform cleaning operations is particularly effective. In certain embodiments, the cavitation engine (e.g., driver, pump, etc.) can be located on a support vessel located on the surface of the water and the underwater robotic vehicle can be connected to the surface support vehicle via a support tether. The cavitation energy can be delivered through the support tether to the underwater robotic vehicle, which can direct the cavitation energy toward the area to be cleaned. The support vehicle can be, for example, a zodiac-type boat or other similar small boat or a surface robotic vehicle/ electric boat. The operation at step 316 can be performed while the robotic vehicle 110 is swimming in the water column and/or after the underwater robot 110 has landed on the undersea surface.

If the underwater robot 110 is still in the swimming configuration, it can land and stabilize on the seafloor at step 318. Transition from a swimming configuration to a landed configuration can be accomplished by disengaging the underwater robot 110 from the surface vehicle/buoyancy module 112/116, as shown in FIGS. 2A-2C and discussed above. Accordingly, a command can be sent to extend the tethers 118 so that the underwater robot 110 lands on the sea floor and the surface vehicle 112 is located on the water surface. As discussed above, the surface vehicle 112 can be used to relay signals between the underwater vehicle 110 and the control station 113. The stabilization on the seafloor can be accomplished by the negative buoyancy of the underwater vehicle 110 providing positive engagement with the seafloor. Thrusters/propellers can also be used to stabilize on the seabed, but they may disturb seafloor sediments and reduce visibility. As such, buoyancy control modules can be used to make the underwater vehicle heavier and stable on the sea bed. The vehicle can also be set to be slightly negatively buoyant in a way that that is heavy enough to stabilize on the sea bed but also light enough to be lifted by the thrusters/propellers, thus eliminating the need for buoyancy control modules in certain configurations. In addition to, or as an alternative to, releasable and/or reusable buoyancy control modules, buoyancy can also be controlled by compressing and/or expanding air inside a container (e.g., ballast tank) and/or moving water and air in and out of a container (e.g., ballast tank). Accordingly, transition from a swimming configuration to a landed configuration can be accomplished by manipulation of the buoyancy module.

At step 320, the tracks 114 can be used to further maneuver the vehicle into position as it is on the seafloor. The tracks/treads 114 can be used to avoid disturbance of sand/silt in the undersea environment, especially in extremely shallow waters.

At step 322, the robotic arm 132 and inspection tool 134 can be used to inspect the operation performed at step 316. The robotic arm 132 can be maneuvered into position so that the inspection tool 134 can perform an inspection operation. At step 324 the inspection can be performed. For example, if the inspection tool is a CP/UT sensor, the weld joint can be inspected using the CP/UT sensor probe. In addition to a camera located on the underwater vehicle 110, another camera can be mounted at the tip of the robotic arm 144 to allow for better visibility of the tip instead of relying on the vehicle camera that it typically far from the long extended end effector of the robotic arm. Accordingly, the second camera can be manipulated into a position that provides an improved monitoring of the inspection sensor (e.g., closer position, better viewing angle, unobstructed position, etc.) A proximity sensor can be used to make sure that the end effector is close to the surface required for inspection. Sonars (1D, 2D and 3D) can also be used for navigating the arm in low visibility area.

At step 326, after cleaning and inspection has been completed at a particular weld joint, the robotic arm 132 can be retracted into a stowed position that is more suitable for the robotic vehicle 110 moving to another position. For example, if the robotic arm 132 was extending during operation, the robotic arm 132 can be folded back into a compact configuration prior to the underwater vehicle 110 moving to another position.

At step 328, the underwater vehicle 110 can move to the next location for further operations (e.g., cleaning and inspection). The vehicle 110 can move by swimming through the water column to the next location. This can be accomplished by reengaging the surface vehicle/buoyancy module 112/116 to provide the vehicle 110 with a net neutral buoyancy and then using thrusters 112 to swim.

Once the vehicle 110 has reached the next desired location (e.g., next weld joint on the underwater pipeline), according to step 330 the cleaning and inspection steps of 316-326 can be repeated. This process can be repeated until all target areas have been operated upon (e.g., all weld joints of the underwater pipeline have been cleaned and inspected).

At step 332, after all operations have been complete, the underwater vehicle 110 can swim to the sea surface. It can then be retrieved, either by swimming to the shore S or swimming to the support vehicle SV.

The steps shown in FIG. 3 are provide the steps according to one embodiment and persons of skill in the art will appreciate that the order of certain steps can be changed and/or certain steps omitted.

As described above, the underwater vehicle 110 can be used to carry the cleaning and inspection modules. In other embodiments, two underwater vehicles can be used and the functions of the underwater vehicle can be split between the two vehicles. For example, one underwater vehicle can be used to perform a cleaning operation and a second underwater vehicle can be used to perform an inspection operation.

In addition to the foregoing description, the embodiment of FIGS. 1-5 can be further described as including the following features. The embodiment discloses a method that can include the step of deploying the underwater robotic vehicle into the water that includes deploying the underwater robotic vehicle from a surface support vessel. The surface support vessel can be a zodiac or a larger boat. Moreover, the steps of performing cleaning operations can include cleaning using cavitation. The system can include a cavitation engine (e.g., cavitation generator) that is supported by a surface boat. The surface boat can be a zodiac, a larger boat, or an electric boat that, on the surface, can follow the underwater vehicle (e.g., the electric boat can be a robotic surface support vessel in certain embodiments).

It should be understood that although much of the foregoing description has been directed to systems and methods for underwater inspection crawlers, the system and methods disclosed herein can be similarly deployed and/or implemented in scenarios, situations, and settings far beyond the referenced scenarios. It should be further understood that any such implementation and/or deployment is within the scope of the system and methods described herein.

It is to be further understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present disclosure need not reside on a single computer or processor, but can be distributed in a modular fashion amongst a number of different computers or processors to implement various aspects of the systems and methods disclosed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

We claim:

1. A method for performing operations on underwater infrastructure at a plurality of locations using a water environment robotic system, comprising steps of:
   a) providing an underwater robotic vehicle at a position proximate the underwater infrastructure;
   b) moving the underwater robotic vehicle through the water to one location of the plurality of locations of the underwater infrastructure;
   c) performing a first operation on the underwater infrastructure at the one location of the plurality of locations;
   d) manipulating the underwater vehicle to engage with a subsea surface by manipulating a buoyancy module to change buoyancy characteristics of the underwater vehicle from neutrally buoyant to negatively buoyant;
   e) performing a second operation on the underwater infrastructure at the one location of the plurality of locations;
   f) moving the underwater robotic vehicle through the water to another location of the plurality of locations of the underwater infrastructure;
   g) repeat steps (c) through (f) until all desired operations are performed at all of the desired locations of the plurality of locations; and
   h) retrieve the underwater vehicle.

2. The method of claim 1, wherein the first operation is a cleaning operation and the second operation is an inspection operation of the previously cleaned first location using a non-destructive sensor.

3. The method of claim 1, wherein the underwater infrastructure is a pipeline and the plurality of locations are weld joints along the pipeline.

4. The method of claim 1, wherein the step of performing a second operation includes the steps of extending a robotic arm and sensing using a non-destructive sensor.

5. A method for performing operations using a water environment robotic system on a target section of pipeline located in an underwater environment, the pipeline having a plurality of weld joints located at a plurality of locations along its length, comprising steps of:
   a) providing an underwater robotic vehicle at a position proximate the underwater pipeline, the underwater robotic vehicle including at least a robotic arm, treads adapted to move the underwater robotic vehicle along a subsea surface, a sensor, and a propulsion system adapted to move the underwater robotic vehicle by swimming through the water;
   b) deploying the underwater robotic vehicle into the water;
   c) visually inspecting the underwater environment to locate the pipeline and its plurality of weld joints using the underwater robotic vehicle;
   d) performing a cleaning operation at one of the plurality of weld joints using underwater robotic vehicle;
   e) manipulating the underwater robotic vehicle to land and stabilize on a subsea surface;
   f) adjusting the position of the underwater robotic vehicle on the subsea surface;
   g) deploying the robotic arm to inspect the cleaned weld joint;
   h) inspecting the cleaned weld joint using the sensor to collect cathodic protection and ultrasonic testing data;

i) stowing the robotic arm into a folded position suitable for the underwater robotic vehicle to swim through the water;

j) causing the underwater robotic vehicle to swim through the water along the pipe line to another of the plurality of weld joints while performing a visual inspection;

k) repeating steps (d) through (j) on multiple weld joints within the target section of the pipeline;

l) causing the underwater robotic vehicle to swim upward; and m) permitting retrieval of the underwater robotic vehicle at a surface of the water environment.

6. The method of claim 5, wherein the step of deploying the underwater robotic vehicle into the water includes deploying the underwater robotic vehicle from a surface support vessel.

7. The method of claim 5, wherein the step of deploying the underwater robotic vehicle into the water includes deploying the underwater robotic vehicle from an onshore location and using the treads to crawl along the subsea surface until the underwater robotic vehicle moves to a position in which the water has a sufficient depth to permit swimming of the underwater robotic vehicle.

8. The method of claim 5, wherein the underwater robotic vehicle is connected to a communication relay that is configured to permit aerial communication between the underwater robotic vehicle and a remote control station.

9. The method of claim 5, further including the step of locating the pipeline using a sonar sensor mounted below the surface support vessel.

10. The method of claim 5, further including the step of locating the pipeline using a sonar sensor mounted on the underwater robotic vehicle.

11. The method of claim 5, wherein the step of performing a cleaning operation includes using at least one of a cavitation system and a brushing system.

12. The method of claim 11, wherein the cavitation system includes a cavitation engine supported by a surface boat.

13. The method of claim 5, wherein the step of manipulating the underwater vehicle to land and stabilize on a subsea surface includes engaging the propulsion system to provide a downward force toward the subsea surface.

14. The method of claim 13, wherein the brushing system includes systems having destabilization reduction means for reducing forces caused during the step of performing a cleaning operation.

15. The method of claim 5, wherein the step of adjusting the position of the underwater robotic vehicle on the subsea surface includes using propellers.

16. The method of claim 5, wherein the step of adjusting the position of the underwater robotic vehicle on the subsea surface includes using the treads to minimize disturbance to the underwater environment.

17. The method of claim 5, wherein the underwater robotic vehicle includes a buoyancy control module, and wherein the step of manipulating the underwater robotic vehicle to land and stabilize on a subsea surface includes using the buoyancy control module to provide the underwater robotic vehicle a negative net buoyancy characteristic.

18. The method of claim 17, wherein the buoyancy control module includes at least one of a releasable float device, a container in which air is capable of being compressed, and a container into which air and water capable of being introduced and removed.

19. The method of claim 5, wherein the underwater robotic vehicle includes a buoyancy control module, further including the step of using the buoyancy control module to provide the underwater robotic vehicle a net neutral buoyancy characteristic prior to the step of swimming through the water along the pipe line to another of the plurality of weld joints.

20. The method of claim 5, wherein the underwater robotic vehicle has a negative net buoyancy characteristic sufficient for stabilization on the subsea surface and also sufficient for swimming through the water using the propulsion system.

21. The method of claim 5, wherein the underwater robotic vehicle includes a first video camera.

22. The method of claim 21, wherein the underwater robotic vehicle includes a second video camera supported by the robotic arm to provide improved monitoring of the inspection sensor.

23. The method of claim 5, wherein the underwater robotic vehicle includes at least one of a proximity sensor and a sonar sensor, supported by the robotic arm.

24. The method of claim 5, wherein the underwater robotic vehicle supports a cleaning module and an inspection module.

25. The method of claim 5, wherein the underwater robotic vehicle includes first and second underwater robotic vehicles, wherein one of the first and second underwater robotic vehicles executes the step of performing a cleaning operation at one of the plurality of weld joints, and the other of the first and second underwater robotic vehicles executes the step of inspecting the cleaned weld joint using the sensor to collect cathodic protection and ultrasonic testing data.

26. A method for performing operations on underwater infrastructure at a plurality of locations using a water environment robotic system, comprising steps of:

a) providing an underwater robotic vehicle at a position proximate the underwater infrastructure;

b) moving the underwater robotic vehicle through the water to one location of the plurality of locations of the underwater infrastructure;

c) performing a first operation on the underwater infrastructure at the one location of the plurality of locations;

d) manipulating the underwater vehicle to engage with a subsea surface by manipulating a buoyancy module to change buoyancy characteristics of the underwater vehicle;

e) performing a second operation on the underwater infrastructure at the one location of the plurality of locations;

f) moving the underwater robotic vehicle through the water to another location of the plurality of locations of the underwater infrastructure by reengaging the underwater vehicle with the buoyancy module to change the buoyancy characteristics of the underwater vehicle from negatively buoyant to neutrally buoyant and moving through the water;

g) repeat steps (c) through (f) until all desired operations are performed at all of the desired locations of the plurality of locations; and h) retrieve the underwater vehicle.

27. The method of claim 26, wherein the first operation is a cleaning operation and the second operation is an inspection operation of the previously cleaned first location using a non-destructive sensor.

28. The method of claim 26, wherein the step of performing a second operation includes the steps of extending a robotic arm and sensing using a non-destructive sensor.

* * * * *